United States Patent
Mohr

(10) Patent No.: US 8,696,200 B2
(45) Date of Patent: Apr. 15, 2014

(54) METHOD FOR AUTOMATICALLY POSITIONING AN X-RAY SOURCE OF AN X-RAY SYSTEM AND X-RAY SYSTEM

(75) Inventor: Cecile Mohr, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 703 days.

(21) Appl. No.: 12/724,637

(22) Filed: Mar. 16, 2010

(65) Prior Publication Data

US 2010/0239070 A1      Sep. 23, 2010

(30) Foreign Application Priority Data

Mar. 17, 2009   (DE) .......................... 10 2009 013 572

(51) Int. Cl.
*H05G 1/02* (2006.01)

(52) U.S. Cl.
USPC .......................................... 378/196; 378/197

(58) Field of Classification Search
USPC .......................................... 378/196, 197, 205
See application file for complete search history.

(56) References Cited

U.S. PATENT DOCUMENTS

| | | | |
|---|---|---|---|
| 6,106,152 A | 8/2000 | Thunberg | 378/205 |
| 6,302,580 B1 | 10/2001 | Dwyer, Jr. et al. | 378/197 |
| 6,435,715 B1 | 8/2002 | Betz et al. | 378/197 |
| 6,859,521 B2 | 2/2005 | Spahn | 378/117 |
| 7,192,188 B2 | 3/2007 | Maschke | 378/197 |
| 7,197,112 B2 | 3/2007 | Maschke | 378/91 |
| 7,432,807 B2 | 10/2008 | Schmitt | 340/568.1 |
| 7,622,889 B2 | 11/2009 | Spahn | 320/101 |
| 2002/0150214 A1 | 10/2002 | Spahn | 378/189 |
| 2003/0194056 A1* | 10/2003 | Spahn | 378/205 |

FOREIGN PATENT DOCUMENTS

| | | |
|---|---|---|
| DE | 19956670 | 5/2000 |
| DE | 19855213 | 6/2000 |
| DE | 10118745 | 10/2002 |
| DE | 10216857 | 11/2003 |
| DE | 102004042063 | 10/2005 |
| DE | 102005027220 | 12/2006 |
| DE | 10344364 | 6/2007 |
| EP | 0856282 | 8/1998 |

OTHER PUBLICATIONS

German Office Action for Application No. 10 2009 013 572.3 (4 pages), Oct. 1, 2009.
Spahn et al. "Flachbilddetektoren in der Rontgendiagnostik" Zeitschrift Radiologe 43, 2004, pp. 340-350; Magazine; 2004 (11 pages), May 1, 2003.

* cited by examiner

*Primary Examiner* — Irakli Kiknadze
(74) *Attorney, Agent, or Firm* — King & Spalding L.L.P.

(57) ABSTRACT

In the interest of a particularly quick and simple X-ray examination, provision is made for a method for automatically positioning a positionable X-ray source (16) of an X-ray system (24) in respect of a mobile X-ray detector (15) with the following steps: —detecting the position of the mobile X-ray detector (15), —forwarding the position to the X-ray system (24), —determining a position of the X-ray source (16), aligned with the position of the mobile X-ray detector (15), for recording an X-ray image, and —driving the positionable X-ray source (16) to move into the aligned position.

14 Claims, 1 Drawing Sheet

METHOD FOR AUTOMATICALLY POSITIONING AN X-RAY SOURCE OF AN X-RAY SYSTEM AND X-RAY SYSTEM

CROSS-REFERENCE TO RELATED APPLICATIONS

This application claims priority to German Patent Application No. 10 2009 013 572.3 filed Mar. 17, 2009, the contents of which is incorporated herein by reference in its entirety.

TECHNICAL FIELD

The invention relates to a method for automatically positioning an X-ray source of an X-ray system and an X-ray system for carrying out such a method.

BACKGROUND

For recording X-ray images of an examination object, X-ray detectors, designed as solid-state detectors, are known in digital X-ray imaging, in which detectors X-ray radiation is converted into electric charge by a scintillator or a direct-converter layer and subsequently read out electronically by means of active readout matrices. The image data representing the examination results are subsequently transmitted to an evaluation and display apparatus and further processed for generating an image (Article "Flachbilddetektoren in der Röntgendiagnostik" [Flat-panel detectors in X-ray diagnostics] by M. Spahn, V. Heer, R. Freytag, published in the journal Radiologe 43, 2004, pages 340 to 350).

By way of example, DE 101 18 745 C2 has disclosed mobile X-ray detectors, which can be positioned anywhere in space and independently of an associated X-ray system. Such X-ray detectors can be connected by wires or be wireless. In such X-ray systems, it is conventional for an operator to position the X-ray source manually relative to the X-ray detector after the X-ray detector has been positioned such that an X-ray image can be recorded.

SUMMARY

According to various embodiments, a method can be provided that ensures simple and quick positioning of the X-ray source. Moreover, according to further embodiments, a suitable X-ray system for carrying out the method can be provided.

According to various embodiments, a method for automatically positioning a positionable X-ray source of an X-ray system in respect of a mobile X-ray detector, may comprise the following steps:
  detecting the position of the mobile X-ray detector,
  forwarding the position to the X-ray system,
  determining a position of the X-ray source, aligned with the position of the mobile X-ray detector, for recording an X-ray image, and
  driving the positionable X-ray source to move into the aligned position.

According to a further embodiment, the position and the orientation of the X-ray detector can be detected and forwarded. According to a further embodiment, at least one of a predetermined distance between the X-ray source and the X-ray detector, a predetermined area of the X-ray detector to be acquired, and a predetermined X-ray dose can be used for determining the aligned position. According to a further embodiment, a predetermined relative position of the X-ray source with respect to the X-ray detector can be used for determining the aligned position and an absolute position of the X-ray source in space is determined from the relative position and used as aligned position on the basis of the position of the X-ray detector.

According to another embodiment, an X-ray system may be operable to carry out a method as stated above, with
  a positionable X-ray source, wherein the X-ray source can be adjusted by means of a positioning apparatus,
  a mobile X-ray detector, wherein the X-ray detector has a position determining apparatus for determining its position,
  a communication link between the X-ray detector and the X-ray system,
  an apparatus for determining an aligned position of the X-ray source in respect of the X-ray detector, and
  an apparatus for driving the X-ray source to move into the aligned position by means of the positioning apparatus.

According to a further embodiment, the X-ray system may have a system control designed to accept the position of the X-ray detector, to determine the position of the X-ray source, aligned with the position of the mobile X-ray detector, for an X-ray, and to drive the X-ray source to move into the aligned position by means of the positioning apparatus.

According to a further embodiment, the position determining apparatus may have position sensors. According to a further embodiment, the position determining apparatus may have at least one imaging apparatus. According to a further embodiment, the X-ray source may have a control apparatus designed to accept the position of the X-ray detector, determine the position of the X-ray source, aligned with the position of the mobile X-ray detector, for an X-ray, and drive the X-ray source to move into the aligned position by means of the positioning apparatus. According to a further embodiment, the mobile X-ray detector may be formed by a mobile flat-panel detector. According to a further embodiment, the mobile X-ray detector can be wireless and may have transmission and reception means for wireless communication, in particular via radio or bluetooth. According to a further embodiment, the mobile X-ray detector may have a wired connection to the X-ray system. According to a further embodiment, the positioning apparatus can be formed by a robot arm on which the X-ray source is arranged.

BRIEF DESCRIPTION OF THE DRAWINGS

The invention and further advantageous refinements as per the features of the dependent claims are explained in more detail in the following text on the basis of exemplary embodiments illustrated schematically in the drawing, without this limiting the invention to these exemplary embodiments. In the figures:

DETAILED DESCRIPTION

Figure 1:
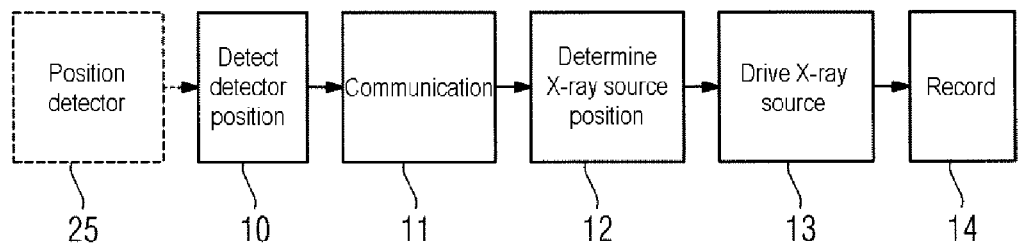
FIG. 1 shows a sequence of steps of the method according to various embodiments and FIG. 2 shows a view of an X-ray system according to various embodiments with a mobile X-ray detector.

According to various embodiments, a method for automatically positioning a positionable X-ray source of an X-ray system in respect of a mobile X-ray detector, comprising the following steps:
  detecting the position of the mobile X-ray detector,
  forwarding the position to the X-ray system, in particular to a system control of the X-ray system, determining a position of the X-ray source, aligned with the position of the mobile X-ray detector, for recording an X-ray image, and driving the positionable X-ray source to move into the aligned position, quickly and simply brings the X-ray source into an ideal position, relative to the X-ray detector, for recording an X-ray image automatically and without input from an operator. This significantly reduces the time expenditure for an X-ray examination. Moreover, reliably good recording of X-ray images can be ensured in any case because the quality of the adjustment of the X-ray source no longer depends on the capabilities of the respective operator. The operability of an X-ray system with a mobile X-ray detector is simplified and the work for the operator is significantly reduced.

Expediently, it is not only the general position but the complete position, i.e. the bearing and orientation of the X-ray detector as well, that is detected and forwarded. This affords particularly good alignment of the X-ray source in respect of the X-ray detector.

According to one refinement, a predetermined distance between the X-ray source and the X-ray detector and/or a predetermined area of the X-ray detector to be acquired and/or a predetermined X-ray dose are used for determining the aligned position. These predetermined values afford particularly quick and simple automatic positioning. By way of example, before the positioning is initiated, an operator can also enter what organ or region of the human body is intended to be recorded. Accordingly, depending on the organ or the region, individual values for the distance, the area or the X-ray dose thus can be predetermined and so particularly high quality of the respective X-ray image is ensured.

According to a further refinement, a predetermined relative position of the X-ray source with respect to the X-ray detector is used for determining the aligned position and an absolute position of the X-ray source in space is determined from the relative position and used as aligned position on the basis of the positional information of the X-ray detector. The predetermined relative position can be stored in the X-ray system and recalled when needed. By way of example, empirical values can be used for this, which according to experience have exhibited a particularly high image quality.

For carrying out the method according to various embodiments, provision is made for an X-ray system, with a positionable X-ray source, wherein the X-ray source can be adjusted by means of a positioning apparatus; a mobile X-ray detector, wherein the X-ray detector has a position determining apparatus for determining its position; a communication link between the X-ray detector and the X-ray system; an apparatus for determining an aligned position of the X-ray source in respect of the X-ray detector; and an apparatus for driving the X-ray source to move into the aligned position by means of the positioning apparatus. Such an X-ray system independently puts the X-ray source into an ideally aligned position for recording an X-ray image after positioning the mobile X-ray detector, and therefore a quick and simple X-ray examination of a patient is ensured. The X-ray detector can be wireless or have a wired connection to the X-ray system.

According to a refinement, the X-ray system has a system control designed to accept the position of the X-ray detector; determine the position of the X-ray source, aligned with the position of the mobile X-ray detector, for an X-ray; and drive the X-ray source to move into the aligned position by means of the positioning apparatus. It is understood that these objects also can be assumed by various units; however, the system control allows the method to be carried out particularly compactly and quickly.

The position determining apparatus advantageously has one or more position sensors for reliably determining the position. If there are a plurality of position sensors, these can be arranged at various positions on the X-ray detector in order to allow a complete detection of the position. Additionally, provision can be made for a unit that determines the absolute position of the X-ray detector in space from the information of the position sensors.

According to a further refinement, the position determining apparatus has at least one imaging apparatus, in particular one or more cameras. Correspondingly calibrated cameras also can be used to determine the position of the X-ray detector.

According to a further refinement, the X-ray source has a control apparatus designed to accept the position of the X-ray detector; determine the position of the X-ray source, aligned with the position of the mobile X-ray detector, for an X-ray; and drive the X-ray source to move into the aligned position by means of the positioning apparatus. Arranging the control apparatus directly on the X-ray source allows a particularly quick and efficient procedure.

The mobile X-ray detector advantageously is formed by a mobile flat-panel detector for recording high-quality X-ray images.

According to a further refinement, the mobile X-ray detector is wireless and has transmission and reception means for wireless communication, for example via radio or bluetooth. Such a mobile, wireless X-ray detector can be brought into any position with respect to a patient without any problems.

Expediently, the mobile X-ray detector has a wired connection to the X-ray system and so quick and error-free communication between the X-ray detector and a component of the X-ray system differing therefrom is ensured.

According to a further refinement, the positioning apparatus is formed by a robot arm on which the X-ray source is arranged. Such a robot arm allows a particularly variable adjustability of the X-ray source. Alternatively, the positioning apparatus can also be formed by, for example, a telescoping arm, which can be displaced on the ceiling by means of rails.

Figure 2:
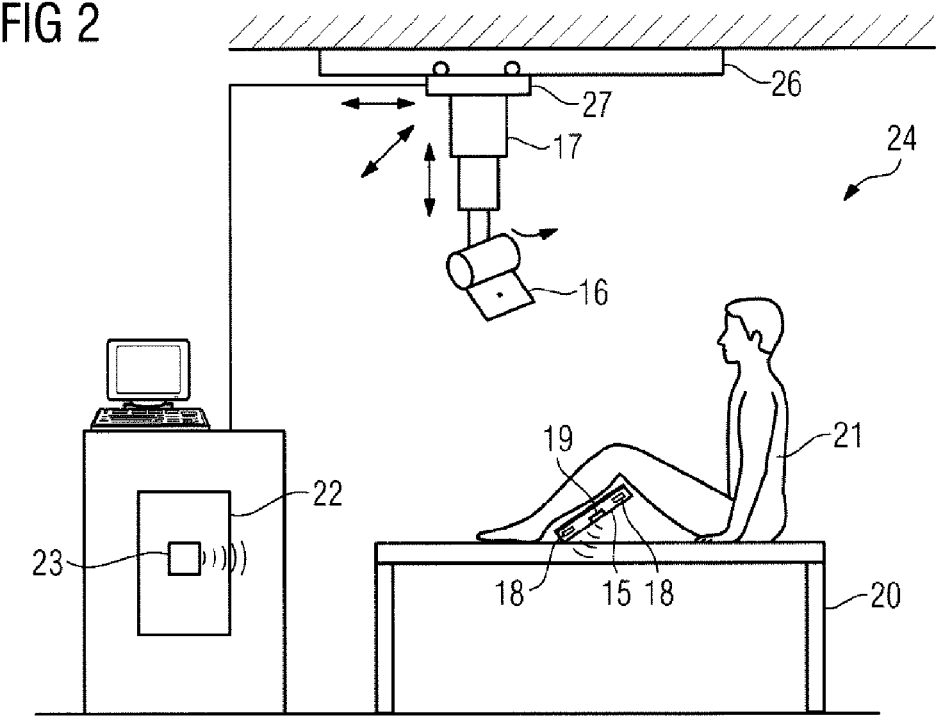

FIG. 2 shows an X-ray system 24, designed to carry out the method according to various embodiments. The X-ray system 24 has a mobile X-ray detector 15, which has position sensors 18 and transmission and reception means 19 for wireless, bidirectional data transfer, in particular to a system control 22 of the X-ray system 24. By way of example, the position sensors can be arranged, respectively on the front side and rear side, on all four corners of the X-ray detector to ensure complete detection of position and bearing.

The X-ray detector 15 is merely associated with the X-ray system 24, but generally does not have a mechanical connection to the other components of the X-ray system. However, provision can be made for the X-ray system for example to have a charging station into which the X-ray detector can be inserted when not in use and in which it can be charged with energy. Provision can also be made for the X-ray detector 15 to have a wired connection to the X-ray system for data transfer. The X-ray detector manually can be positioned anywhere in respect of a patient 21 by an operator in order to record X-ray images of an organ or body part of the patient 21.

The X-ray system 24 also has an X-ray source 16, generally an X-ray emitter with an anode and a cathode, for generating X-ray radiation. The X-ray source 16 is arranged on a positioning apparatus, e.g. a telescoping arm 17, which can be displaced along a ceiling of the examination room in different directions by motor-control by means of a carriage 27 on rails or wheels. The telescoping arm 17 allows upward and downward motion and tilting of the X-ray source 16. By way of example, the X-ray source can also be arranged on a robot arm and it can be moved—three-dimensionally in space—and adjusted in an automatically driven fashion by means of said robot arm. The positioning apparatus can also have a different type of support and can be moved or adjusted in a different known fashion.

A system control 22 is provided for driving the X-ray system 24. The system control moreover has a transmission and reception means 23 for data transfer, in particular with the X-ray detector 15. Additionally, the X-ray system generally has an image system for processing X-ray images, an input unit for entering commands of an operator, a monitor for displaying recorded X-ray images and a generator for generating high voltage for the X-ray source.

FIG. 1 shows the sequence of steps of the method according to various embodiments in an exemplary fashion. Starting from a manual positioning of the X-ray detector (step 25) by an operator, the position of the X-ray detector 15 is determined automatically (step 10). The position is determined by means of, for example, the position sensors or another position determining apparatus according to known measurement principles, e.g. by means of GPS, triangulation or radio. Herein, the absolute position of the X-ray detector in space in particular is determined; however, it is also possible to determine a relative position of the X-ray detector in respect of a calibration object.

The precise orientation and bearing of the X-ray detector in space is advantageously determined. Herein, the information in respect of on what side of the X-ray detector the active area is situated is also important.

Once the position and the bearing of the X-ray detector are known, this information is forwarded to the X-ray system, in particular to the system control 22 or to another control unit (step 11).

In the next step (step 12), a position of the X-ray source, aligned for recording a high-quality X-ray image, is determined on the basis of the position and/or bearing and orientation of the X-ray detector. By way of example, this determination can be determined by means of a calculating unit, a computer, or by means of the system control. In the process, the aligned position of the X-ray source can for example be determined by the absolute position of the X-ray source in space being calculated for a predetermined position and bearing relative to the X-ray detector. Such predetermined positions can be stored in a storage unit and can be used, if needed, for determining the aligned position.

The aligned position can also be determined on the basis of, for example, an algorithm or an approximation by means of various individual predetermined values such as, for example, a predetermined distance between the X-ray source and the X-ray detector and/or a predetermined area of the X-ray detector to be acquired and/or a predetermined X-ray dose. Here, the predetermined values or predetermined positions can be based on empirical values for particularly good-quality X-ray images. Here, the empirical values in each case can depend on the organ or body part of the patient to be recorded. The organ or body part to be recorded can be entered by an operator before the X-ray examination starts. In particular, the aligned position to be assumed by the X-ray source is determined from the position of the X-ray detector by means of further information. For this, it is generally also necessary to know the current position of the X-ray source.

Once the aligned position of the X-ray source has been determined, the positioning apparatus 17 of the X-ray source is driven in order to move the X-ray source 16 into the aligned position (step 13). Once the X-ray source 16 is in the aligned position, one or more X-ray images can subsequently be recorded (step 14).

By way of example, the method can be initiated when the X-ray system is switched on and/or it can be repeated at regular intervals so that the X-ray source is always ideally aligned with respect to the mobile X-ray detector.

The various embodiments can briefly be summarized as follows: In the interest of a particularly quick and simple X-ray examination, provision is made for a method for automatically positioning an X-ray source 16 of an X-ray system 24 in respect of a mobile X-ray detector (15), comprising the following steps:
  detecting the position of the mobile X-ray detector 15,
  forwarding the position to the X-ray system 24,
  determining a position of the X-ray source 16, aligned with the position of the mobile X-ray detector 15, for recording an X-ray image, and
  driving the X-ray source 16 to move into the aligned position.

What is claimed is:

1. A method for automatically positioning a positionable X-ray source of an X-ray system with respect to a mobile X-ray detector, comprising:
  detecting the position of the mobile X-ray detector,
  forwarding the position of the mobile X-ray detector to the X-ray system,
  calculating an aligned position of the X-ray source based on the forwarded position of the mobile X-ray detector, the aligned position being different than a current position of the X-ray source and defining a position of the X-ray source relative to the position of the mobile X-ray detector for recording an X-ray image, and
  automatically driving the positionable X-ray source to move from the current position of the X-ray source to the calculated aligned position of the X-ray source.

2. The method according to claim 1, wherein the position and the orientation of the X-ray detector are detected and forwarded.

3. The method according to claim 1, wherein at least one of a predetermined distance between the X-ray source and the X-ray detector, a predetermined area of the X-ray detector to be acquired, and a predetermined X-ray dose are used for calculating the aligned position.

4. The method according to claim 1, wherein a predetermined relative position of the X-ray source with respect to the X-ray detector is used for calculating the aligned position and an absolute position of the X-ray source in space is determined from the relative position and used as aligned position on the basis of the position of the X-ray detector.

5. An X-ray system for automatically positioning a positionable X-ray source of an X-ray system with respect to a mobile X-ray detector, comprising:
  a positionable X-ray source configured for adjustment by a positioning apparatus,
  a mobile X-ray detector comprising:
    a position determining apparatus configured to determine a position of the X-ray detector, and
    a transmitter configured to forward the position of the mobile X-ray detector to a control system via a communication link between the X-ray detector and the control system,
  an apparatus configured to calculate an aligned position of the X-ray source based on the forwarded position of the mobile X-ray detector, the aligned position being different than a current position of the X-ray source and defining a position of the X-ray source relative to the X-ray detector, and an apparatus configured to automatically drive the X-ray source to move from the current position of the X-ray source to the calculated aligned position of the X-ray source by the positioning apparatus.

6. The X-ray system according to claim 5, wherein the position determining apparatus has position sensors.

7. The X-ray system according to claim 5, wherein the position determining apparatus has at least one imaging apparatus.

8. The X-ray system according to claim 5, wherein the X-ray source has a control apparatus operable to
   accept the position of the X-ray detector,
   determine the position of the X-ray source, aligned with the position of the mobile X-ray detector, for an X-ray, and
   drive the X-ray source to move into the aligned position by the positioning apparatus.

9. The X-ray system according to claim 5, wherein the mobile X-ray detector comprises a mobile flat-panel detector.

10. The X-ray system according to claim 5, wherein the mobile X-ray detector is wireless and the transmitter is configured for wireless communication or via radio or bluetooth.

11. The X-ray system according to claim 5, wherein the mobile X-ray detector has a wired connection to the control system.

12. The X-ray system according to claim 5, wherein the positioning apparatus is formed by a robot arm on which the X-ray source is arranged.

13. A system for automatically positioning a positionable X-ray source of an X-ray system with respect to a mobile X-ray detector, comprising:
   a positionable X-ray source configured for adjustment by a positioning apparatus,
   an automated control system configured to:
      receive from the mobile X-ray detector, via a communication link between the X-ray detector and the control system, position information regarding a position of the X-ray system,
      calculate an aligned position of the X-ray source based on the received position information of the mobile X-ray detector, the aligned position being different than a current position of the X-ray source and defining a position of the X-ray source relative to the X-ray detector, and
      automatically drive the X-ray source to move from the current position of the X-ray source to the calculated aligned position of the X-ray source by the positioning apparatus.

14. The system according to claim 13, wherein the an automated control system configured to receive the position information from the mobile X-ray detector via wireless communications.

* * * * *